(12) United States Patent
Roland

(10) Patent No.: US 7,609,062 B2
(45) Date of Patent: Oct. 27, 2009

(54) MAGNETIC RESONANCE DEVICE WITH A PATIENT SUPPORT TABLE AND A MAIN FIELD MAGNET

(75) Inventor: Jörg Roland, Gremsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/642,797

(22) Filed: Dec. 20, 2006

(65) Prior Publication Data
US 2007/0145979 A1    Jun. 28, 2007

(30) Foreign Application Priority Data
Dec. 22, 2005    (DE)    ................. 10 2005 061 558

(51) Int. Cl.
*G01V 3/00*    (2006.01)

(52) U.S. Cl. .................. 324/318; 600/415; 324/319

(58) Field of Classification Search ......... 324/318–319; 600/400, 415
See application file for complete search history.

(56) References Cited

U.S. PATENT DOCUMENTS

| | | | | |
|---|---|---|---|---|
| 5,423,315 A | * | 6/1995 | Margosian et al. | 600/410 |
| 5,436,607 A | * | 7/1995 | Chari et al. | 335/216 |
| 5,517,121 A | * | 5/1996 | Kaufman et al. | 324/319 |
| 5,615,430 A | * | 4/1997 | Nambu et al. | 5/600 |
| 5,735,278 A | * | 4/1998 | Hoult et al. | 600/422 |
| 6,241,671 B1 | * | 6/2001 | Ritter et al. | 600/427 |
| 6,373,251 B1 | * | 4/2002 | Damadian et al. | 324/318 |
| 6,806,712 B2 | * | 10/2004 | Akgun | 324/318 |
| 6,812,702 B2 | * | 11/2004 | Yoshino et al. | 324/318 |
| 7,057,389 B2 | * | 6/2006 | Kamimura et al. | 324/318 |

FOREIGN PATENT DOCUMENTS

| | | |
|---|---|---|
| JP | 61114148 A | 5/1986 |
| JP | 2001 046355 A | 2/2001 |
| WO | WO 01/70109 | 9/2001 |

\* cited by examiner

*Primary Examiner*—Brij B. Shrivastav
*Assistant Examiner*—Megann E Vaughn

(57) ABSTRACT

Magnetic resonance device comprises a patient support table and a main field magnet. The main field magnet is supported so that it can be rotated around at least one axis. The patient support table is able to be rotated around an axis essentially perpendicular in respect of its table surface.

20 Claims, 2 Drawing Sheets

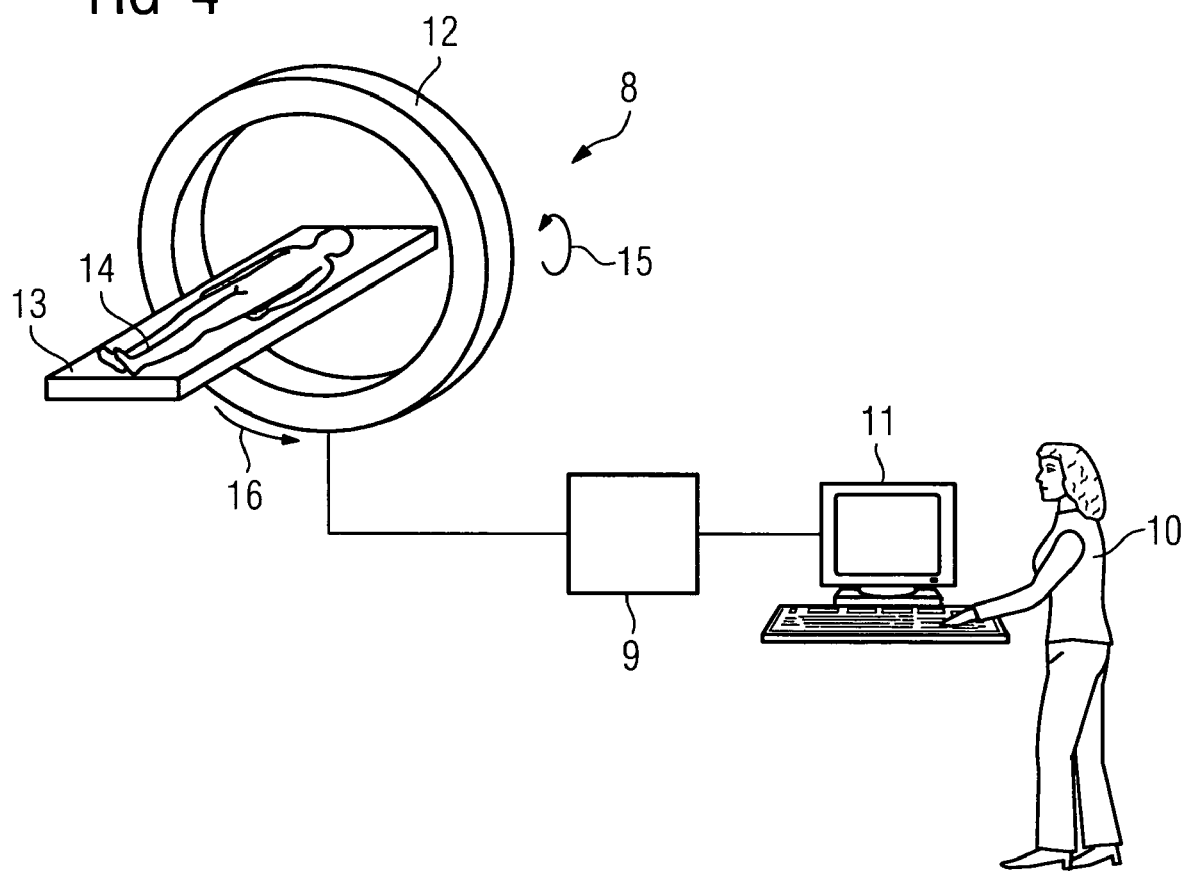

MAGNETIC RESONANCE DEVICE WITH A PATIENT SUPPORT TABLE AND A MAIN FIELD MAGNET

CROSS REFERENCE TO RELATED APPLICATIONS

This application claims priority of German application No. 10 2005 061 558.9 filed Dec. 22, 2005, which is incorporated by reference herein in its entirety.

FIELD OF THE INVENTION

The invention relates to a magnetic resonance device with a patient support table and a main field magnet, with the main field magnet being supported so that it can be rotated around at least one axis.

BACKGROUND OF THE INVENTION

Ever greater attempts have been made in recent times with magnetic resonance scanners, under the impetus of technical development in computer tomography, to use shorter main field magnets in order to thereby achieve a more open embodiment of magnetic resonance devices. Such shortening of the magnets for magnetic resonance scanners offers the advantage that access to the patient is facilitated during production of image recordings or when performing measurements and between individual recordings. In addition a patient's feeling of claustrophobia or even feelings of anxiety which frequently occur during the examination can be avoided. In addition, the shorter embodiment of the magnet in the z-direction, i.e. in the direction of the longitudinal axis of a patient support table, counters the increasing cost pressures arising during manufacturing of the scanners, since the scanner costs are definitively determined by the magnet costs. These magnet costs can be significantly reduced by a reduction of the material and a simplification of the magnet structure.

Despite innovative construction concepts for the magnets or the magnetic resonance devices, making the magnet shorter is frequently connected with a shortening of the area with a homogeneous magnetic field. This has meant that in recent times there has been evidence, with a number of newer systems, of a markedly shorter field-of-view available for image recording.

The shortening of the area with a homogeneous magnetic field in the z-direction produces problems however, if tilted or even double-tilted layers are to be recorded, as is required for example for spinal cord images and specific heart images. With an extreme shortening of the magnet the homogeneous magnetic field area available in the z-direction is no longer sufficient here under some circumstances to produce measurements with the required quality and expressiveness.

An arrangement for magnetic resonance imaging is known from WO 01/70109 A1, in which the opening has a diameter which is significantly greater than the axial length of the opening. After the patient has been placed in the opening, a relative rotation between the patient and the magnet arrangement can be undertaken, for the purposes of which the magnet arrangement is tilted or rotated respectively around a horizontal axis or the patient is subjected to a corresponding horizontal inclination or rotation, as is indicated for example in FIGS. 6 to 13 of this document.

JP 2001 046355 A relates to a device for creating a magnetic field, in which a rotational force can be exerted on a horizontal axis. A rotation actuator can also be used to exert a rotational impulse on a vertical axis which is connected to a support arm.

A device for creating a magnetic field is known from JP 611 141 148 A in which a linear motor is provided for movement of the magnet arc.

SUMMARY OF THE INVENTION

The object of the invention is thus to specify a magnetic resonance device which is improved in this respect.

To achieve this object the invention provides, for a magnetic resonance device of the type mentioned at the start, for the patient support table to be rotatable around an axis essentially perpendicular to its table surface.

For a magnetic resonance device with a short main field magnet, that is a magnet with a length in the z-direction which is less, in some cases markedly less than the current normal length of 1.30 m, the rotatable support still enables a recording of tilted layers to be made. What are involved here are main field magnets with a length in the range of one meter or less, whereby magnets with a length in the range of a few tens of centimeters, for example in the range of 30 cm, are to be viewed as the target of current technical development. Whereas with the usual earlier magnets the field-of-view extends over around 40 cm, with an extreme shortening of the longitudinal axis of the magnet to 30 cm for example, there is only likely to be a field-of-view of for example 10 cm in the z-direction. In the x- and y-direction on the other hand the field-of-view extends by contrast over a greater area.

The rotatability of the main field magnet around at least one and if necessary a number of axes makes a reduction of the homogeneity area of the magnetic resonance scanner possible, without allowance having to be made for detrimental affects regarding the quality of the image recordings. The rotatability easily allows operation with a very short field-of-view, so that the magnets can be further shortened in relation to today's usual magnets, resulting in considerable costs savings during manufacturing. In addition a significant advantage is obtained for marketing the products, especially with regard to the desired better access to patients e.g. for interventions. More complicated magnetic resonance images are still possible, with the comfort for the patient being able to be greatly enhanced by the greater openness with a short magnet.

In addition the patient support table can be rotated around its essentially perpendicular axis in relation to its table surface, especially around an axis running through the center of the magnetic field. Such a rotation of the table can generally be implemented comparatively easily. The rotatability or the tilting around two different axes, positioned at right angles to one another for example, according to the system of axes used in the anatomy, is required for specific measurements of double tilted layers with a very short magnet, for example for specific spinal column and heart images. Thus the rotatability of the main field magnets, preferably around a horizontal axis, is advantageously supplemented by a rotation of the patient support table, which can at its simplest be undertaken around a perpendicular axis, so that no problems occur in respect of a patient sliding off or changing position. If a number of axes of rotation or tilt axes are provided in different directions, these are expediently arranged so that they feature, at least approximately, an intersection point. This obtains an optimum expansion of the pivoting options.

The main field magnet can be embodied as a short magnet in the longitudinal direction of the patient support table.

In accordance with the invention the main field magnet is able to be rotated around at least one axis essentially horizontal in relation to the table surface of the patient support table of the magnetic resonance device, especially around an axis running through the center of the magnetic field. A swiveling or tilting of the magnet is especially worthwhile around a horizontal axis running through the longitudinal axis of the magnet, which with usual magnetic resonance devices runs a little above the support table, i.e. in the area of the patient supported on it. This means that an optimum variability is produced as regards the options for recording measurements in respect of the positioning of the patient. Of course it is also possible, especially with magnetic resonance devices which are predominantly or exclusively used for very specific imaging tasks, to provide axes which run outside the center of the magnetic field or are not arranged to be entirely horizontal. The desired deviation from the horizontal alignment of the axis is determined in such cases by the requirements imposed on the movability of the magnet for optimum image recording.

The main field magnet can, especially on both sides, be rotatable by up to 30° around the essentially horizontal axis. The ability to rotate on both sides, as seen by a patient who is located on the support table, i.e. towards them or away from them, makes flexible recording of tilted layers possible. The value of 30° is to be seen here as a typical value by which a magnet which may be shortened to 30 cm can be tilted with a normal support without collisions between components and without patient comfort being adversely affected. Naturally the widest possible degree of rotation is desirable, which is only limited by the demands on the integration of the individual components of the magnetic resonance device or by the length of the main field magnet. With a corresponding embodiment of the support, of the magnet and where necessary of further components, an ability to be rotated by more than 30° in at least one direction is conceivable.

The patient support table can be rotated, especially on both sides by up to 43° around the essentially perpendicular axis. The value is to be seen as typical for a rotation that can be implemented, with a maximum rotatability of 45° or more of course to be seen as desirable. The limits are predetermined by the constructional options and the adaptation of the dimensions of the support or of the magnet.

Furthermore the main field magnet can be rotatable around at least one essentially perpendicular axis in relation to the table surface of the patient support table of the magnetic resonance device, especially around an axis running through the center of the magnetic field. This means that it is conceivable, simply by rotating the magnet around different axes, independently of the ability to rotate the table, to provide good facilities for recording doubly tilted layers. The orientation of the second axis can deviate from the perpendicular to cater for specific image recording requirements. It is thus also conceivable for example to provide an ability to rotate around more than two axes or an ability to rotate around axes which neither run vertically nor horizontally. Where necessary the ability to rotate the magnet around two different axes can also be supplemented by a table which is capable of rotation, especially around a vertical axis. In principle it is possible to support the main field magnet on a gimbal mount to achieve maximum mobility.

In accordance with the invention the main field magnet can be mounted on the ceiling side with the aid of attachment means, especially a suspension unit. A suspension unit, especially in the form of the idea of a floating magnetic resonance device or a floating magnet, offers the advantage of degrees of freedom of movement, whereas with a rigid mounting an appropriate means of adjustment is to be provided which allows rotational movement of the magnet.

The patient support table can be attached adjustably with the aid of attachment means to the main field magnets such that the patient support table remains in its position if the main field magnet is rotated and if necessary conversely the main field magnet remains in its position if the patient support table is rotated. Thus, if necessary with the aid of corresponding adjustable attachment means, a separate table mount can be dispensed with, in which case the ability of the magnet or of the table to be rotated, especially with intersecting pivot axes, is unimpeded by the restrictions imposed by a separate mount. In this case however it should be ensured for recording the tilted layers that where the magnet is rotated or in the case in which a rotation of the table is intended, the other part remains in its position in each case or is able to be moved decoupled from the rotational movement of the other part. If necessary a corresponding adjustment of the attachment means can be undertaken using a control device such that the desired rotation of the magnet and/or of the table is obtained taking into account the relative positions required for this.

Of course, as an alternative or in addition, a separate table mount which can if necessary be detached in this case can be provided, especially in at least one end area of the patient support table. The mount is in this case to be embodied to allow rotation of the patient table such that a displacement relative to the axis of rotation is possible. A table mount at the end or in the end area of the patient support table is preferable, so as not to restrict the rotation of the magnet in the middle area of the patient table. Naturally the patient support table can be supported to as to allow movement in its longitudinal direction.

The patient support table can be tiltable around at least one axis, especially one disposed horizontally to the surface of the table. Naturally tilting around an only approximately horizontal or angled axis can be provided as an alternative. When the table surface is tilted it should be ensured that the patient remains securely supported or the positioning of the patient is not negatively affected. Thus tilting can only be undertaken slowly and not by too extreme an angle. The patient support table can further be moved lengthwise through the magnet for recording greater volumes even when recording imaging data (measurement) is taking place, if necessary even in a previously assumed tilted position.

The main field magnet can, in its non-rotated position in the longitudinal direction of the patient support table, have a length of less than one meter, especially a length of less than 50 cm. The main field magnet thus has a short longitudinal axis of less than one meter. Even with a main field magnet with a length in the range of one meter or slightly less, better access to a patient is obtained by comparison with current magnetic resonance devices. With a further shortening, for example to 50 cm or below, the comfort for the patient during the examination can be greatly enhanced while making it easier for those undertaking the examination to monitor the patient or intervene where necessary between measurements or during the measurements.

Furthermore the invention relates to a method for creating images of at least one tilted layer, especially a double tilted layer with a magnetic resonance device, especially a magnetic resonance device as described above, with a patient support table and a main field magnet embodied as a short magnet in the longitudinal direction of the patient support table, in which the main field magnet, for positioning the layer to be recorded in an area with a homogeneous magnetic field, is rotated around at least one axis, especially under software control, if necessary also during a measurement (image recording). In addition the patient support table is rotated around an axis essentially perpendicular in relation to its table surface. Naturally the magnet for imaging of tilted layers, as described above in the context of the magnetic resonance device, can be rotated around a number of axes, especially approximately horizontal and/or vertical axes, with alternatively or in addition to the rotation of the magnet around a number of axes, an ability of the patient support table to be rotated or tilted, also preferably under software control and if necessary during image recording, able to be provided.

Thus in accordance with the invention, even with magnetic resonance devices with very short main field magnets with a length of less than one meter or in the region of half a meter, it is possible to produce more complex images, such as multiply tilted layers.

BRIEF DESCRIPTION OF THE DRAWINGS

Further advantages, features and details of the invention emerge with reference to the following exemplary embodiments and also from the drawings. The Figures show.

DETAILED DESCRIPTION OF THE INVENTION

Figure 1:
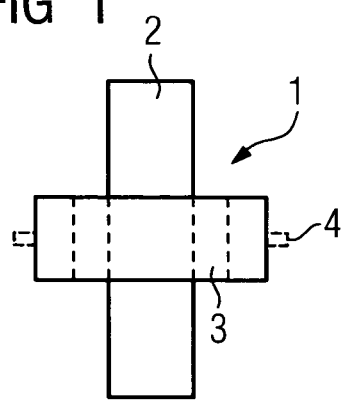
FIG. 1 a view from above of an inventive magnetic resonance device.

FIG. 1 shows a view from above of the inventive magnetic resonance device 1, which, in addition to a patient support table 2, features a main field magnet 3. The other components required for a magnetic resonance device, such as the gradient coil system for example and a corresponding cladding and such like are not shown in this diagram for reasons of clarity. The main field magnet 3, with a length of 30 cm, is embodied as a very short magnet.

To make it possible to record images of the tilted layers despite the markedly shorter field of view in the z-direction caused by the short magnet, the main field magnet 3 of the magnetic resonance device 1 is mounted on a rotatable support, as illustrated here by the virtual axis of rotation 4, which is disposed horizontally in relation to the table surface of the patient support table 2. The virtual axis of rotation 4 thus runs transversally through the body of the patient supported on the patient support table 2 but not shown in this diagram, and is implemented by attachment means or mounts (not shown), which make rotatable support possible.

The patient support table 2 is able to be rotated around an axis essentially perpendicular to its table surface.

Figure 2A:
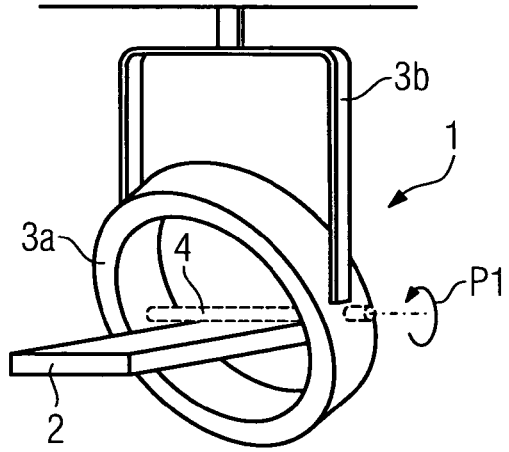
FIGS. 2A+2B examples of rotating the main field magnets of the magnetic resonance device of FIG. 1 around a horizontal axis, FIGS. 3A+3B an inventive magnetic resonance device with a rotatable patient support table, and FIG. 4 a sketch depicting execution of an inventive method.
Figure 2B:
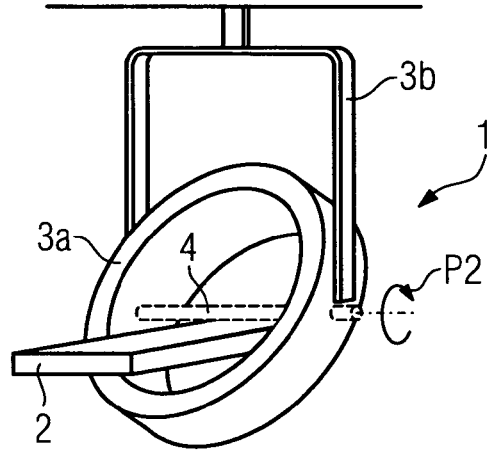

FIGS. 2A and 2B show examples of rotating the main field magnet 3a of the magnetic resonance device 1 of FIG. 1 around the horizontal axis of rotation 4. FIG. 2A here just shows the magnet in relation to the support surface of the patient support table 2 tilted forward in the diagram, with a tilt angle of 30° shown here. FIG. 2B shows a corresponding tilting in the opposite direction, likewise by 30°. This makes it possible, if necessary supplemented by a rotation of the patient support table 2, which is not shown here, to execute demanding measurements for recording tilted layers which are needed for example for diagnostics in the spinal column area. Moving-Table or Move-During-Scan applications are required in such cases as technical prerequisites, to enable a suitable data capture or subsequent processing into images to be performed.

The attachment means 3b are used for mounting the main field magnet 3a on the ceiling of the room in which the magnetic resonance device is installed. The mounting shown is merely to be seen as a schematic diagram. The attachment to the magnet 3a is implemented with a pivot joint to make the tilting shown by the arrows P1 and P2 possible.

Alternatively the main field magnet can be attached in a fixed manner and the degree of freedom to rotate can be provided further towards the ceiling side by a suitable arrangement of appropriate attachment means, for example by using a pivot joint with corresponding adjustment or movement facilities of the rail-type components of the attachment means.

Figure 3A:
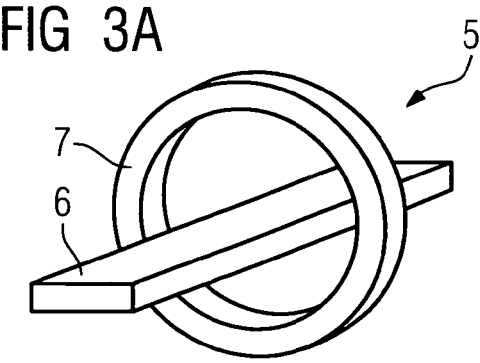
Figure 3B:
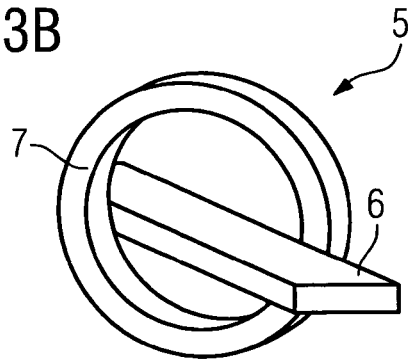

FIGS. 3A and 3B finally show an inventive magnetic resonance device 5 with a rotatable patient support table 6 which can be rotated on both sides around a perpendicular axis not shown in the diagram. The other components of the magnetic resonance device 5 are once again not shown for reasons of clarity.

FIG. 3A shows the patient support table 6 rotated in relation to the main field magnet 7 by 43° in the clockwise direction, whereas in FIG. 3B the corresponding rotation in the counterclockwise direction is shown. The end-side support of the patient table 6 is not shown in the Figure. The ability of the magnet to rotate is limited by the constructional specifications and by patient comfort requirements.

The ability to rotate the patient table 6 supplements the ability to rotate the main field magnet 7 around an axis positioned essentially perpendicular to the axis of rotation of the patient support table 6, which makes it possible to create images with a very short field-of-view for a main field magnet 7 which extends for a very short distance in the longitudinal direction.

FIG. 4 illustrates the execution of an inventive method. The method for creating images of tilted layers is executed in the magnetic resonance device 8, which features a control device 9 to control the imaging process in accordance with inputs made by a user 10 at a combined image output and input means 11. In this case the finished images or the available image logs and such like are displayed to the user 10 at the image input and output means 11.

In addition the magnetic resonance device 8 features a main field magnet 12, into the magnetic field area of which a patient support table 13 can be moved. A patient 14 is supported on the patient support table 13.

If the user 10 selects a recording of tilted layers via the combined image output and input means 11, the patient 14 is brought into the area of the homogeneous magnetic field required for optimum imaging by a rotation of the main field magnet 12, indicated in this diagram by the rotation arrow 15, where necessary supplemented by a rotation of the patient support table 13, indicated by the rotation arrow 16. This allows the area of homogeneity of the scanner to be reduced, which is linked to significant cost savings, without restricting the options for working with respect to the measurements and image recording of the magnetic resonance device 8 to be performed. Thus even complicated magnetic resonance images can be recorded with better accessibility to the patient 14. Instead of the previous usual main field magnets with a weight of for example 2 t shorter main field magnets, such as the main field magnet 12 shown here for example, can be used, which weigh far less and are thus easier to manufacture and to install.

The invention claimed is:

1. A magnetic resonance device used in a medical examination, comprising:

a patient support table that is rotated during performance of an imaging scan by the magnetic resonance device, the table rotated during the performance of the imaging scan around an axis essentially perpendicular to a surface of the patient support table disposed to support a patient; and a main field magnet that is rotated during the performance of the imaging scan by the magnetic resonance device, the magnet rotated during the performance of the imaging scan around a further axis, wherein a rotation of the patient support table around the essentially perpendicular axis is controlled by a controller so that a section of the patient being imaged as the table is rotated remains within an imaging field of view of a rotating magnetic field generated by the main field magnet as the main field magnet rotates around the further axis to record an image of said section of the patient.

2. The magnetic resonance device as claimed in claim 1, wherein a length of the main field magnet in a longitudinal direction of the patient support table is shorter than a normal length of a main field magnet used in a normal magnetic resonance device.

3. The magnetic resonance device as claimed in claim 2, wherein the length of the main field magnet in the longitudinal direction of the patient support table is less than one meter.

4. The magnetic resonance device as claimed in claim 3, wherein the length of the main field magnet in the longitudinal direction of the patient support table is less than half meter.

5. The magnetic resonance device as claimed in claim 1, wherein the further axis around which the main field magnet is rotated is through a center of a magnetic field generated by the main field magnet.

6. The magnetic resonance device as claimed in claim 1, wherein the further axis around which the main field magnet is rotated is essentially horizontal to the surface of the patient support table.

7. The magnetic resonance device as claimed in claim 6, wherein the essentially horizontal axis is in a longitudinal direction of the main field magnet.

8. The magnetic resonance device as claimed in claim 6, wherein the main field magnet is rotated up to 30° on both sides around the essentially horizontal axis.

9. The magnetic resonance device as claimed in claim 1, wherein the patient support table is rotated up to 43° on both sides around the essentially perpendicular axis.

10. The magnetic resonance device as claimed in claim 1, wherein the further axis around which the main field magnet is rotated is essentially perpendicular to the surface of the patient support table.

11. The magnetic resonance device as claimed in claim 1, wherein the main field magnet is rotated around a plurality of axes.

12. The magnetic resonance device as claimed in claim 1, wherein the main field magnet is mounted on a ceiling of an examination room by an attachment device.

13. The magnetic resonance device as claimed in claim 12, wherein the attachment device is a suspension unit.

14. The magnetic resonance device as claimed in claim 1, wherein the patient support table is attached by an attachment device and is adjusted to the main field magnet so that:

the patient support table remains still while the main field magnet is rotated, or the main field magnet remains still while the patient support table is rotated.

15. The magnetic resonance device as claimed in claim 14, wherein the patient support table is mounted on a separate table mount.

16. The magnetic resonance device as claimed in claim 15, wherein the separate table mount is at an end area of the patient support table.

17. The magnetic resonance device as claimed in claim 1, wherein the patient support table is tilted around an axis essentially horizontal to the surface of the patient support table.

18. A method for creating an image of a tilted layer of a patient by a magnetic resonance device, comprising:

rotating a patient support table during performance of an imaging scan by the magnetic resonance device, the rotating of the table being around an axis essentially perpendicular to a surface of the patient support table disposed to support a patient;

providing a main field magnet that is shorter than a normal main field magnet used in a normal magnetic resonance device in a longitudinal direction of the patient support table;

rotating the main field magnet during the performance of the imaging scan by the magnetic resonance device, the rotating of the magnet being around a further axis for positioning the tilted layer in an area of a homogeneous magnetic field;

controlling a rotation of the patient support table around the essentially perpendicular axis so that a section of the patient being imaged as the table is rotated remains within an imaging field of view of a rotating magnetic field generated by the main field magnet as the main magnet rotates to record an image of said section of the patient.

19. The method as claimed in claim 18, wherein an image of a double tilted layer of the patient is recorded by the magnetic resonance device.

20. A magnetic resonance device used in a medical examination, comprising:

a patient support table that is rotated during performance of an imaging scan by the magnetic resonance device, the table rotated during the performance of the imaging scan around an axis essentially perpendicular to a surface of the patient support table disposed to support a patient;

a main field magnet that is rotated during the performance of the imaging scan by the magnetic resonance device, the magnet rotated during the performance of the imaging scan around a further axis; and control means for controlling a rotation of the patient support table around the essentially perpendicular axis so that a section of the patient being imaged as the table is rotated remains within an imaging field of view of a rotating magnetic field generated by the main field magnet as the main field magnet rotates around the further axis to record an image of said section of the patient.

* * * * *